(12) United States Patent
Shen et al.

(10) Patent No.: US 7,952,705 B2
(45) Date of Patent: May 31, 2011

(54) INTEGRATED MICROFLUIDIC OPTICAL DEVICE FOR SUB-MICRO LITER LIQUID SAMPLE MICROSPECTROSCOPY

(75) Inventors: Pao-Lin Shen, Moraga, CA (US); Li Jiang, Moraga, CA (US); Kejung Jiang, Beijing (CN)

(73) Assignee: Dynamic Throughput Inc., Moraga, CA (US)

( * ) Notice: Subject to any disclaimer, the term of this patent is extended or adjusted under 35 U.S.C. 154(b) by 501 days.

(21) Appl. No.: 11/970,451

(22) Filed: Jan. 7, 2008

(65) Prior Publication Data

US 2009/0051901 A1     Feb. 26, 2009

Related U.S. Application Data

(60) Provisional application No. 60/957,984, filed on Aug. 24, 2007.

(51) Int. Cl.
*G01N 1/10* (2006.01)
*G01N 21/00* (2006.01)

(52) U.S. Cl. ......... 356/246; 356/432; 356/326; 356/317

(58) Field of Classification Search ........... 356/244, 356/246, 432, 440, 317, 326
See application file for complete search history.

(56) References Cited

U.S. PATENT DOCUMENTS

| | | |
|---|---|---|
| 4,863,560 A | 9/1989 | Hawkins |
| 5,006,202 A | 4/1991 | Hawkins |
| 5,116,759 A * | 5/1992 | Klainer et al. ........... 435/287.2 |
| 5,738,757 A | 4/1998 | Burns et al. |
| 5,842,787 A | 12/1998 | Kopf-Sill et al. |
| 5,957,579 A | 9/1999 | Kopf-Sill et al. |
| 6,100,541 A | 8/2000 | Nagle et al. |
| 6,123,685 A | 9/2000 | Reynolds |
| 6,490,034 B1 * | 12/2002 | Woias et al. .................. 356/246 |
| 6,800,849 B2 | 10/2004 | Staats |
| 6,867,857 B2 | 3/2005 | Hobbs |
| 6,900,889 B2 | 5/2005 | Bjornson et al. |
| 6,906,797 B1 | 6/2005 | Kao et al. |
| 7,630,073 B2 * | 12/2009 | Lundquist et al. ........... 356/317 |
| 2003/0036206 A1 * | 2/2003 | Chien et al. ................. 436/180 |
| 2004/0005582 A1 | 1/2004 | Shipwash |
| 2004/0033525 A1 | 2/2004 | Monforte et al. |
| 2004/0095579 A1 | 5/2004 | Bisson et al. |
| 2005/0018201 A1 | 1/2005 | De Boer et al. |
| 2005/0244863 A1 | 11/2005 | Mir |
| 2006/0006067 A1 | 1/2006 | Unger |
| 2006/0046277 A1 | 3/2006 | Belyaev et al. |
| 2006/0068412 A1 | 3/2006 | Tang |
| 2006/0084792 A1 | 4/2006 | Paavola et al. |

(Continued)

OTHER PUBLICATIONS

Backlung and Rosengren. New Shapes in (100) SI using KOH and EDP Etches. J. Micromech. Microeng. 2 (1992) 75-79.

(Continued)

*Primary Examiner* — L. G Lauchman
(74) *Attorney, Agent, or Firm* — Karl Bozicevic; Bozicevic, Field & Francis LLP

(57) ABSTRACT

The present disclosure relates to the fields of microchips with microfluidic optical chambers for multiplexed optical spectroscopy. Embodiments of the present invention allow for ultra small sample volume, as well as high detection speed and throughput, as compared to conventional optical sample cuvettes used in optical spectroscopy. Particular embodiments relate specifically to the spectroscopic detection of many biochemical assays for disease diagnosis or other suitable analysis.

3 Claims, 14 Drawing Sheets

U.S. PATENT DOCUMENTS

| | | |
|---|---|---|
| 2006/0115536 A1 | 6/2006 | Yacaman et al. |
| 2006/0189044 A1 | 8/2006 | Shah et al. |
| 2006/0290926 A1 | 12/2006 | Masters et al. |
| 2007/0105339 A1 | 5/2007 | Faris |
| 2009/0009756 A1* | 1/2009 | Yamamichi et al. .......... 356/246 |

OTHER PUBLICATIONS

Chang, S., et al. Mesa structure formation using potassium hydroxide and ethylenediamine based etchants. IEEE Workshop on Solid-State Sensors and Actuators, Jun. 6-9, 1988, Hilton Head, S.C., pp. 102-103.

Resnik, D., et al. The role of Triton surfactant in anisotropic etching of {110} reflective planes on (100) silicon. J Micromech Microeng. 2005, vol. 15, pp. 1174-1183.

Sekimura, M., et al. Fabrication of 45° optical mirrors on (100) silicon using surfactant-added TMAH solution. International Conference on Solid State Sensors and Actuators, Sendai, Japan, Jun. 7-10, 1999, pp. 550-551.

Strandman, C., et al. Fabrication of 45° mirrors together with well-defined V-grooves using wet anisotropic etching of silicon. Journal of Microelectromechanical Systems. 1995, vol. 4, No. 4, pp. 213-219.

* cited by examiner

INTEGRATED MICROFLUIDIC OPTICAL DEVICE FOR SUB-MICRO LITER LIQUID SAMPLE MICROSPECTROSCOPY

RELATED APPLICATIONS

This application claims priority from Provisional U.S. Patent Application 60/957,984 "Integrated Microfluidic Optical Device for Sub-Micro Liter Liquid Sample Microspectroscopy," by Shen, et al., filed on Aug. 24, 2007, which is incorporated herein by reference for all purposes noting that this application controls to the extent of any differences.

TECHNICAL FIELD

The field of the invention is excitation and detection of light emitting, or absorption entities in microchannels and the fabrication of devices for this purpose. Embodiments of the invention relate to the field of microchips with microfluidic optical chambers for multiplexed optical spectroscopy. Advantages include ultra small sample volume, high detection speed, and throughput over the conventional optical sample cuvette used in optical spectroscopy, as well as automated fluidic sample flow and temperature control. This may be applied to the spectroscopic detection of many analytical chemistry applications or biochemical assays for disease diagnosis.

BACKGROUND

Microfluidic devices and systems of such devices employ small capillaries or microchannels attached or integrated with a solid substrate to perform a variety of operations in a number of analytical chemical and biochemical applications on a very small scale. For example, integrated microfluidic devices can first employ electrical fields to effectively separate nucleic acids, proteins or other macromolecules of interest and then use microscale detection systems for characterization and analysis of the separation products. Such microfluidic devices accomplish these operations using remarkably small reaction volumes that can be at least several orders of magnitude smaller than conventional methods. The small size of these systems allows for increased reaction rates that use less reagent volume and that take up far less laboratory or industrial space. Microfluidic systems thus offer the potential for attractive efficiency gains, and consequently, substantial economic advantages.

Microfluidic devices are particularly well-suited to conduct analytical methods that employ spectroscopic detection systems. A variety of spectroscopic techniques can be employed in conjunction with microfluidic devices, including infrared (IR), visible light, ultraviolet (UV), X-ray, microwave, electron beam, ion beam, positron emission, nuclear magnetic resonance (NMR), as well as various adsorption, emission, fluorescence, surface plasmon resonance (SPR), polarization, and light scattering spectroscopy, such as Raman spectroscopy. The particular technique employed will depend on the particular application. In research or industrial settings, microfluidic devices are typically employed in biochemical or cell-based assays that use spectroscopic detection systems to quantify labeled or unlabeled molecules of interest. For example, such an assay measures the expression of green fluorescent protein in mammalian cells following treatment by a candidate small molecule or biologic drug of interest. Another example is the use of the quantitative polymer chain reaction technique (PCR) in microfluidics devices for gene amplification and analysis with intercalating fluorescence dye as the spectroscopic indicator. Other examples include, but are not limited to, enzymatic and biochemical reactions in general, chemical reactions, phase transition detections, etc.

Microfluidic devices generally employ networks of integrated microscale channels and reservoirs in which materials are transported, mixed, separated and detected, with various detectors and sensors embedded or externally arranged for quantification, as well as actuators and other accessories for manipulations of the fluidic samples. The development of sophisticated material transport systems has permitted the development of systems that are readily automatable and highly reproducible. Such operations are potentially automatable and can be incorporated into high-throughput systems with tremendous advantages for numerous industrial and research applications. Microfluidic devices often use plastics as the substrate. While polymeric materials offer advantages of easy fabrication, low cost and availability, they tend to be fluorescent. For example, when irradiating a sample with excitation light, light scatter may result in a significant background signal, particularly when the excitation pathway and emission pathway are the same. Other materials, such as glass, silicon, and metal may be used as well.

BRIEF DESCRIPTION OF RELEVANT ART

U.S. Patents of interest include U.S. Pat. No. 4,863,560, "Fabrication of Silicon Structures by Single Side, Multiple Step Etching Process"; U.S. Pat. No. 5,006,202, "Fabrication Method for Silicon Devices Using a Two Step Silicon Etching Process"; and U.S. Pat. No. 5,738,757, "Planar Masking for Multi-Depth Silicon Etching." Publications of interest include Backlund and Rosengren, "New shapes in (100) Si using KOH and EDP etches," *J. Micromach. Microeng.* 1992, 2:75-79; Sekimura and Naruse, Fabrication of 45° optical mirrors on (100) silicon using surfactant-added TMAH solution," *International Conference on Solid State Sensors and Actuators*, pp. 550-551, Sendai, Japan, Jun. 7-10, 1999; Strandman, et al., "Fabrication of 45° Mirrors Together with Well-Defined V-grooves Using Wet Anisotropic Etching of Silicon, *J. of Microelectromechanical Systems* (*MEMS*) and Chang and Hicks, "Mesa structure formation using potassium hydroxide and ethylene diamine based etchants." *IEEE Workshop on Solid State Sensors and Actuators*, pp. 102-103, Hilton Head, S. C., June 1988; Resnik et al, "The role of Triton surfactant in anistropic etching of 110 reflective plans on 100 silicon," J. of Micromech. Microeng. 15, 1174-1183 (2005).

SUMMARY OF THE INVENTION

Methods and devices are provided for an optical system for emission detection from microchannels in silicon or plastic substrates. The silicon device can be formed by separately etching different microstructures with appropriate masking and different protective coatings and layers, which may be individually removed prior to final etching to provide deep microstructures. The device can accommodate parallel fluid streams, optionally separated with at least substantially perpendicular or slanted side walls, and on each side of the streams is, e.g., a microfabricated optic with reflecting walls for directing a light beam through the streams and then into a waste light dump. For molding with polymeric materials, the silicon device may be replicated twice and used with polymers to obtain a desired result. Microfabrication techniques are provided for molding microfluidic devices employing the optical system for use in fluorescent based operations.

The present invention demonstrates an integrated microscale chamber with sub-micro liter volume for standard optical spectroscopy such as absorption spectroscopy, fluorescence spectroscopy, photoluminescence spectroscopy, Raman spectroscopy, circular dichroism, etc. The microscale optical chamber has two integrated 45° or other suitable angle reflectance surfaces allowing the light coupling to external optics. The optical path length of the microscale chamber can be shorter or even longer than that of the conventional optical cuvette used for absorption and fluorescence measurements (usually at 1 cm), but the volume may be smaller than 1 µL. The longer light path can allow for greater sensitivity in absorbance detection. The shorter light path can allow for further miniaturization of the detection module in the chip. The absorption is significant to be detectable by a spectrometer camera but the required volume can be more than 1000 times smaller than that used in conventional spectroscopy. The microscale dimension of the optical chamber can enable integration of multiple individual optical chambers in one chip, so a multiplexed optical spectroscopy of 2, 3, 8, 16, 32, 48, 96, 192, 384, 768, and even 1536 samples can be accomplished using a single device which holds all the samples at once.

Accordingly, present embodiments of the invention present high sensitivity biomolecule detection on a chip with simultaneous detection of absorbance/fluorescence spectrums. The fluidic sample flow and reaction temperature in the microscale chamber may be controlled by external electronics, and/or mechanical micro-pumps. Due to the relatively small volume of the microchip and the fluidic sample, the flow rate and heating/cooling rate can be orders of magnitude higher than bulk scale counterparts, which enable many special applications, such as on-chip PCR and fast fluidic exchange.

Compared to the prior art, the claimed subject matter involves monolithically fabricated optical detection chambers, which also serve the purpose of the microfluidic chamber. In this way, the optical detection of microfluidic biological and chemical samples can be implemented in the same device without the need for further assembly with other microdevices. In addition, the unique three optical window design claimed herein allows for the detection of multiple optical spectra such as absorption, transmission, fluorescence, scattering and many other spectra.

BRIEF DESCRIPTION OF THE DRAWINGS

Embodiments of the invention are best understood from the following detailed description when read in conjunction with the accompanying drawings. It is emphasized that, according to common practice, the various features of the drawings are not to-scale. On the contrary, the dimensions of the various features are arbitrarily expanded or reduced for clarity.

DETAILED DESCRIPTION OF THE PREFERRED EMBODIMENTS

Figure 1:
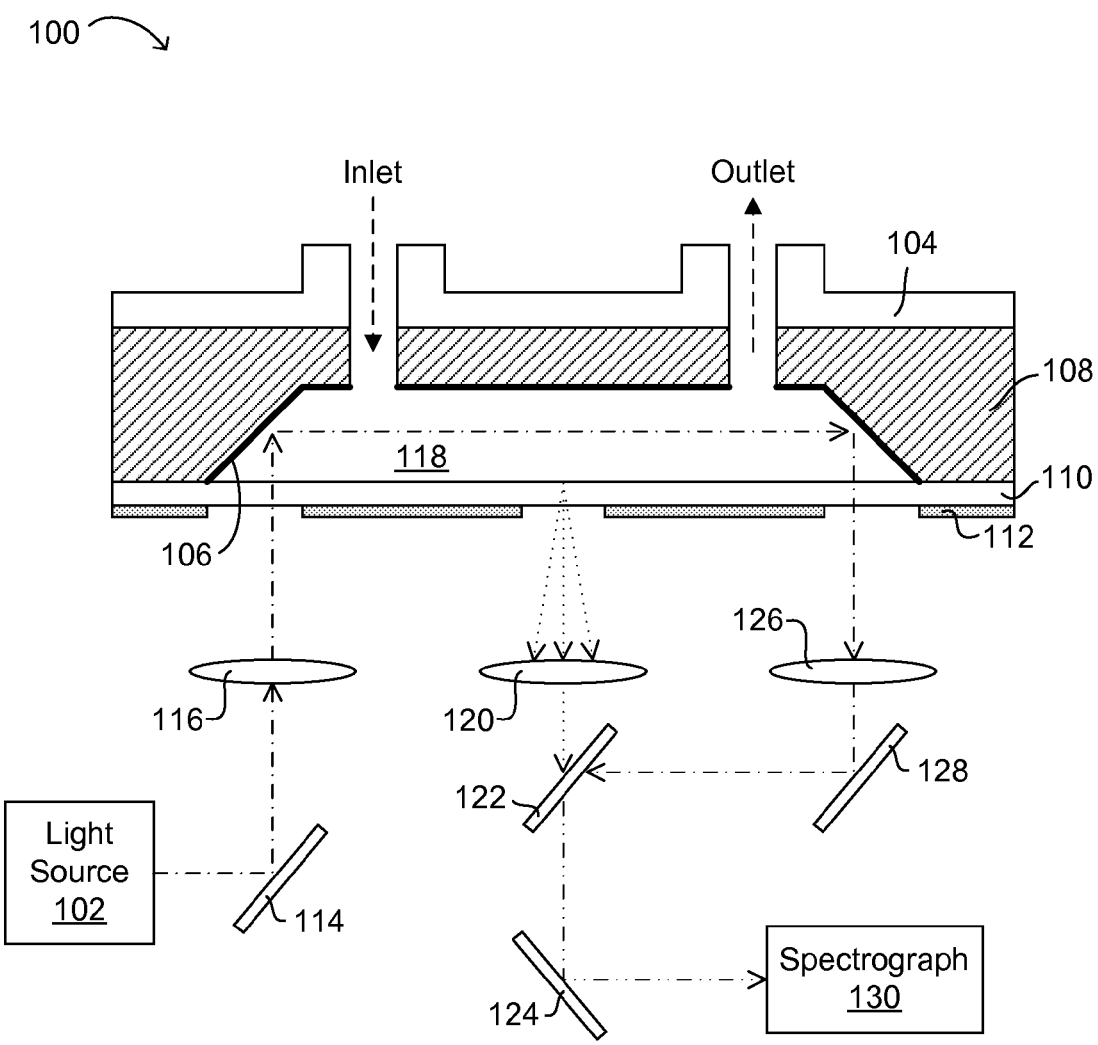
FIG. 1 shows an example system configuration with a microfluidics optical device and detection apparatus in accordance with embodiments of the present invention.

Before the methods and devices of embodiments of the present invention are described, it is to be understood that the invention is not limited to any particular embodiment described, as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent there is a contradiction between the present disclosure and a publication incorporated by reference.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Conventionally, a chemical or biological sample must be in a cuvette for optical spectroscopic analysis. The present invention is based on the discovery that it is possible to shrink such cuvettes down onto chips (e.g., cut from silicon wafers) to create an optical path giving an absorption spectrum and/or a fluorescence spectrum of the sample. The resulting design may be considered an array of "on-chip microcuvettes."

Nanostructures may be fabricated on the surface of the microfluidics channel to provide enhancement of optical signals or substrate to anchor detection probes or to capture target molecules or particulates for detection. Molecular probes, such as antibodies, aptamers, DNA or RNA oligonucleotide and longer probes, peptides, polysaccharides, polymers, small molecules, etc., can be chemically linked to the surfaces of the microfluidic chamber in the chip, which can increase the detection specificity and expand potential applications. The molecular probes may also be tethered to physically fabricated nanostructures to create nanobio hybrid probes in the microfluidic chamber.

Embodiments of the technology presented herein have applications in, inter alia, diagnostic tests or molecular diagnostics. For example, molecular diagnostics, and in particular molecular diagnostics that detect biomarkers related to cancer, measure biomarkers including small molecule metabolites or metabolic intermediates, nucleic acids, carbohydrates, proteins, protein fragments, protein complexes or derivatives or combinations thereof. Chemical assays and in particular analytical methods that employ spectroscopic detection systems may be used in the detection and quantification of such biomarkers, and may provide information about the interaction of biomarkers with test molecules such as small molecules, enzymes, carbohydrates, nucleic acid probes, nucleic acid or protein aptamers, peptide nucleic acids, peptides, or polyclonal or monoclonal antibodies. Such assay methods may be employed initially during the identification, characterization, and development of molecular diagnostics, and may also be employed as molecular diagnostic tests used to assay biological samples and thus measure the health status of patients or to provide information that may support medical decisions. Particular embodiments also have applications in, inter alia, molecular therapeutics. For example, identification and characterization of drug targets may involve detection and quantification of such drug targets in biological samples. Chemical assays and analytical methods that employ spectroscopic detection systems may be used to detect and quantify potential drug targets including proteins such as cell surface proteins, extracellular proteins, peptide hormones, transmembrane proteins, receptor proteins, signaling proteins, cytosolic proteins or enzymes, nuclear proteins, DNA-binding proteins, RNA molecules including messenger RNA or micro-RNAs, or DNA. Such assays and methods may also provide information about the interaction of drug targets with drugs such as small molecules, polyclonal or monoclonal antibodies, therapeutic proteins or therapeutic enzymes, antisense nucleic acids, small-interfering RNAs, nucleic acid or protein aptamers, peptide nucleic acids, or other drugs and potential drugs. Such assay methods may be employed initially during the identification, characterization, and development of molecular therapeutics, and may also be employed in tests to identify individual patients' responsiveness to treatment with drugs or potential drugs, and thus provide valuable information that may support medical decisions.

The terms "nucleic acid" and "polynucleotide" are used interchangeably herein to refer to deoxyribonucleotides or ribonucleotides, and polymers thereof, in either single- or double-stranded form. The terms generally encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

The terms "polypeptide," "peptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, e.g., an α carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Further, silicon wafers are preferable to conventional antibody affinity binding assay substrates that can only detect concentration. Other semiconductor wafers (e.g., GaAs, InP, GaP, GaSb, InSb, InAs, $CaF_2$, $LaAl2O3$, $LiGaO2$, MgO, SrTiOq, YSZ and ZnO) can also be used in certain embodiments. Suitable semiconductor materials for the wafer include, but are not limited to, elements of Groups II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, etc.) and III-V (GaN, GaP, GaAs, GaSb, InN, InP, InAs, InSb, etc.) and IV (Ge, Si, etc.) groups on the periodic table, and alloys or mixtures thereof. Suitable metals and metal oxides for the surface coating include, but are not limited to, Au, Ag, Co, Ni, $Fe_2O_3$, $TiO_2$, and the like. Suitable carbon nanoparticles for surface coating include, e.g., carbon nano-spheres, carbon nano-onions, carbon nanotubes, and fullerene.

In particular embodiments, enzymatic activity and protein concentration may also be detected. In the context of prostate tumors, for example, whereas prostate-specific antigen (PSA) concentration can now be detected, it may not be clear whether the antigen is active or not, possibly providing a misleading measurement. An aspect of certain embodiments includes generating information regarding not only concentration, but also activity. Further, particular embodiments also include a detection system in lieu of a chip scanner.

A system for liquid sample microspectroscopy in certain embodiments may generally include a detection apparatus (e.g., instrumentation portion) coupled to a microfluidics optical device (e.g., a chip or integrated circuit (IC) portion). The detection apparatus can include a light source for sending light through a liquid sample to be characterized, and a spectrograph and/or analysis unit to analyze the light (e.g., fluorescence, absorbance, etc.) affected by molecules of the sample. The microfluidic optical device can be fabricated using semiconductor processing techniques, and may be packaged to protect the semiconductor therein and to accommodate inlet/outlet ports for the liquid sample.

"Biological sample" as used herein is a sample of biological tissue or chemical fluid that is suspected of containing an analyte of interest. Samples include, for example, body fluids such as whole blood, serum, plasma, cerebrospinal fluid, urine, lymph fluids, and various external secretions of the respiratory, intestinal and genitourinary tracts such as tears, saliva, semen, milk, and the like; and other biological fluids such as cell culture suspensions, cell extracts, cell culture supernatants. Samples may also include tissue biopsies, e.g., from the lung, liver, brain, eye, tongue, colon, kidney, muscle, heart, breast, skin, pancreas, uterus, cervix, prostate, salivary gland, and the like. A sample may be suspended or dissolved in, e.g., buffers, extractants, solvents, and the like. A sample can be from any naturally occurring organism or a recombinant organism including, e.g., viruses, prokaryotes or eukaryotes, and mammals (e.g., rodents, felines, canines, and primates). The organism may be a nondiseased organism, an organism suspected of being diseased, or a diseased organism. A mammalian subject from whom a sample is taken may have, be suspected of having, or have a disease such as, for example, cancer, autoimmune disease, or cardiovascular disease, pulmonary disease, gastrointestinal disease, muscoskeletal disorders, central nervous system disorders, infectious disease (e.g., viral, fungal, or bacterial infection). The term biological sample also refers to research samples which have been deliberately created for the study of biological processes or discovery or screening of drug candidates. Such examples include, but are not limited to, aqueous samples that have been doped with bacteria, viruses, DNA, polypeptides, natural or recombinant proteins, metal ions, or drug candidates and their mixtures.

Referring now to FIG. 1, an example system configuration with a microfluidics optical device and detection apparatus in accordance with embodiments of the present invention is shown and indicated by the general reference character 100. Light source 102 can provide a beam that is reflected using mirror 114, and that can pass via lens 116 for focusing and input to microfluidic optical chamber 118 via an optically transparent opening. Light source 102 can provide an illumination/excitation light beam that may be any suitable form of light, such as white light, laser light (e.g., visible laser, ultraviolet (UV) laser, near infrared laser etc.), light emitting diode (LED), super luminescent diode, polarized light, halogen lamp-generated light, continuous or pulsed Xenon Lamp, Mercury light source, Argon light source, Deuterium light source, Tungsten light source and Deuterium-Tungsten-Halogen mixed light source, etc. Generally, the microfluidic optical chamber can be populated by molecules of a liquid or sample to be characterized, where the liquid is received via the inlet port, and can also be discharged via the outlet port.

Incoming light (e.g., focused via lens 116) can be reflected in microfluidic optical chamber 118 using reflective coating 106. For example, reflective coating 106 can be aluminum, gold, silver, chromium, multilayer dielectrics or any suitable reflective metal, or non-reflective material (which can still be used to measure surface plasmon resonance (SPR)), or nanomaterial (e.g., nano-fibers, nanoparticles, nanocoating, nanopatterns, etc.). Multilayer composite material reflective coating can be made on the side wall as a narrow bandwidth reflector.

The semiconductor surface may further include a hydrophilic coating (e.g., a coating of hydrophilic materials or stabilizing groups) to enhance the hydrophilicity of the semiconductor surface, so as to facilitate the entrance of the liquid sample into the microchannel. Suitable hydrophilic materials include, e.g., SiO, $SiO_2$, polyethylene glycol, ether, mecapto acid and hydrocarbonic acid, and dihydroxylipoic acid (DHLA). In particular embodiments, the hydrophilic coating is a silica layer (e.g., including $SiO_2$). Typical methods of silanizing semiconductor surfaces can also be used. Suitable stabilizing groups include, e.g., positively or negatively charged groups or groups that facilitate steric repulsion. Other suitable strategies for generating water-soluble semiconductor surface can be employed as well.

Once the light is passed through microfluidic optical chamber 118, absorbance can occur via objective lens 126, with reflection off mirror 128, and sending to beam splitter 122. Also, fluorescence can emanate from microfluidic optical chamber 118, may be received via optical lens 120, and passed to beam splitter 122. From beam splitter 122, light can be reflected using mirror 124 for receipt in spectrograph 130. Spectrograph 130 may also include a charge coupled device (CCD) for analysis of the various wavelengths contained in the received light beam.

In this fashion, one or more characteristics of the sample found in chamber 118 can be determined based on analysis of received fluorescence and/or absorbance light in spectrograph 130. Further, and as will be discussed in more detail below, the microscale dimensions of the optical chamber presented herein can allow for integration of multiple individual optical chambers in one chip, such that the multiplexed optical spectroscopy of 2, 96, and even 384 samples, can be accomplished.

Generally, certain embodiments can include an instrumentation portion discussed above, as well as an IC portion. The IC portion can include semiconductor material 108, with via-holes therein to accommodate inlet and outlet ports as shown, and polymer bounding layer 104 covering the semiconductor material 108. Semiconductor material 108 can include any suitable semiconductor material, such as silicon (Si), germanium, silicon dioxide, gallium arsenide (GaAs), etc. Suitable semiconductor materials for the wafer include, but are not limited to, elements of Groups II-VI (ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, etc.) and III-V (GaN, GaP, GaAs, GaSb, InN, InP, InAs, InSb, etc.) and IV (Ge, Si, etc.) groups on the periodic table, and alloys or mixtures thereof. Further, transparent window 110 can isolate the IC portion from the instrumentation portion, and material 112 (e.g., silicon dioxide, polydimethylsiloxane (PDMS), coc polymer, or any UV transparent plastics) can be utilized to coat transparent window 110 to define optically transparent openings or through channels for light.

In certain embodiments, inlet and outlet ports need not be aligned with the through channels for light, but rather may be placed to accommodate other connections and/or pathways for fluid ingress/egress. In addition, because certain embodiments can include placing the optical apparatus or instrumentation portion on the opposite chip side (e.g., the bottom side) relative to inlet/outlet channels (e.g., the top side), there is substantial leeway as to placing the inlet and outlet channels without interfering with the optical analysis aspects. Further, sizes of the inlet and outlet channels or ports can be varied, and may thus provide a filtering function by allowing for different sample volumes, molecule sizes, etc., depending upon the particular application.

In particular embodiments, the shape of microfluidic optical chamber 118 can be other than straight, such as serpentine or spiraled. In addition, fluorescence and scattering spectra can alternatively be collected not strictly from reflective mirrors, but also from the entire channels as all-direction fluorescence and scattering light emissions. Semiconductor fabrication can generally be done using existing semiconductor processing techniques, thus allowing for high-volume production. In this fashion, the IC portion of the microfluidic optical device can be manufactured.

FIGS. 2A-2E show example cross-sectional views of semiconductor processing steps for forming a microfluidic optical device in accordance with embodiments of the present invention. First, photolithography can be used to pattern the backside of the semiconductor wafer (see, e.g., FIG. 2A). Single crystal silicon 202 can be arranged with the '100' silicon surface facing down, as shown. Photoresist 204 can be patterned as shown to allow for subsequent etching of silicon 202 in areas not protected by photoresist 204. This step can define an extent of an elongated length of optical chamber 118.

Figure 2A:
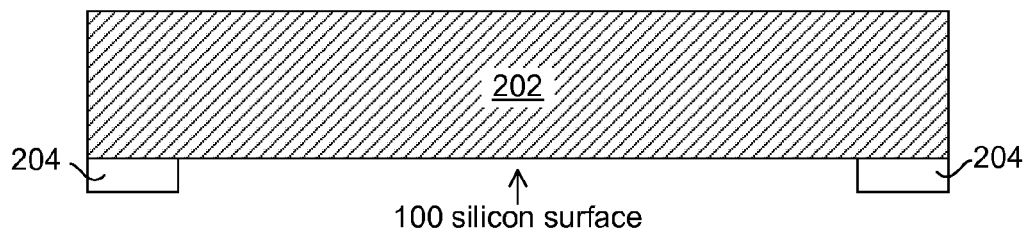
FIGS. 2A-2E show cross-sectional views of example semiconductor processing steps for forming a microfluidic optical device in accordance with embodiments of the present invention.
Figure 2B:
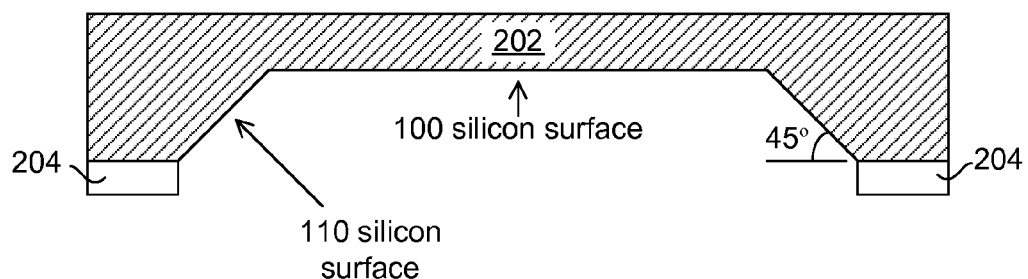

FIG. 2B shows a cross-section view after etching the backside using patterned photoresist 204. For example, wet etching using an alkaline etchant can be used for this process. As shown, the resulting silicon surfaces exposed include the '100' silicon surface, as well as the '110' silicon surface at about a 45° angle. Also in particular embodiments, the reflectivity and reflective spectrum of the etched '110' silicon surface can be modified by depositing a metallic layer including any suitable material and thickness. Further, other surfaces (e.g., the '111' silicon surface) can be also used as the reflective surface, where an associated adjustment can be made to about a 53.7° angle relative to the elongated length.

Figure 2C:
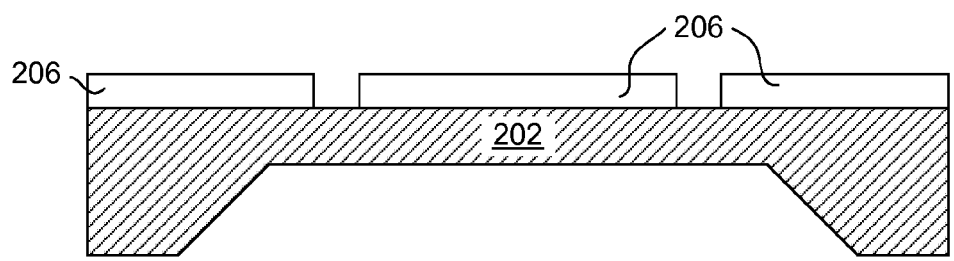
Figure 2D:
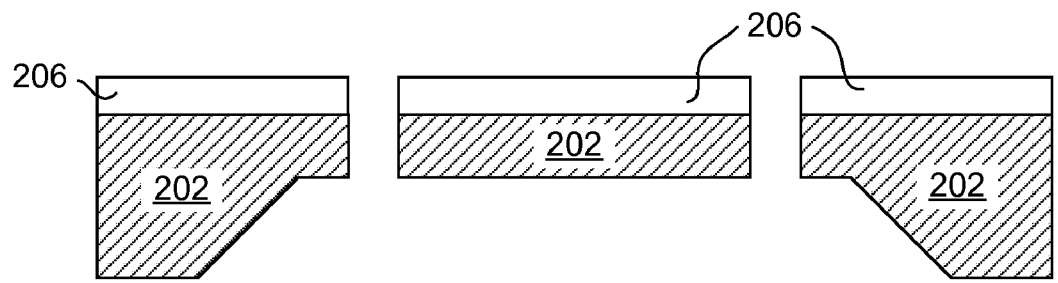

In FIG. 2C, photolithography can be used to pattern in the wafer frontside by utilizing patterned photoresist 206 to define holes or channels for coupling to inlets/outlets. Via-holes can be etched through the silicon above the through channel area, as shown in FIG. 2D. In one embodiment, these via-holes may have a diameter or width of about 100 µm. Of course, any suitable width for these via-holes (e.g., within ranges of from about 80 µm to about 120 µm, or from about 50 µm to about 150 µm) can be utilized in particular embodiments. For example, these via-hole widths may also be configured to form a filtering function, such as by disallowing larger molecules from flowing into the through channel or chamber.

Further, the location of the via-holes can be varied, as discussed above. For example, the locations of these via-holes may be beyond the micro channel, as shown below in FIGS. 6 and 11. In this case, the via-hole opening on the microfluidics channel side may not affect the integrity of the optical chamber, especially the reflective surfaces.

Figure 2E:
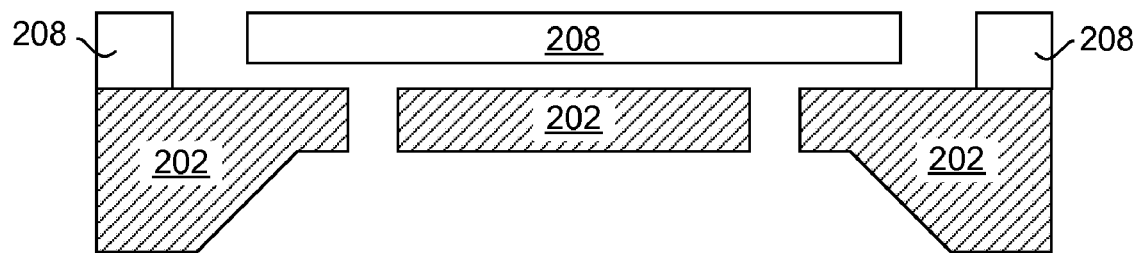

FIG. 2E shows an example application of polymer bounding layer 208 over silicon areas 202 to accommodate inlet and outlet channels.

In one embodiment, two mirrors oriented at about 45° may also be fabricated at each end of the chamber. The microscale optical chamber is typically between about 0.1 and 5 cm long, between about 20 and 500 µm in width and between about 10 and 250 µm in depth (see e.g., chamber 118 shown in FIG. 1). Although any of a range of optical chamber sizes might be especially well suited for each particular application, preferred embodiments include an optical chamber of about 2 cm long, 200 µm in width and 100 µm in depth. The mirror surfaces can be monolithically fabricated together with the microscale optical chamber using a wet silicon etching method. Since the micro channels can be aligned at about 45° with respect to the major flat or elongated length of the '100' silicon wafer, the end surfaces of the micro chambers are '110' silicon surfaces oriented at about 45° with respect to the '100' silicon wafer surface. After wet etching to make the 45° angles exposing '100' silicon surfaces, an aluminum (Al) layer having a thickness of about 100 nm may be deposited on the surface to create the reflective mirrors.

Figure 3:
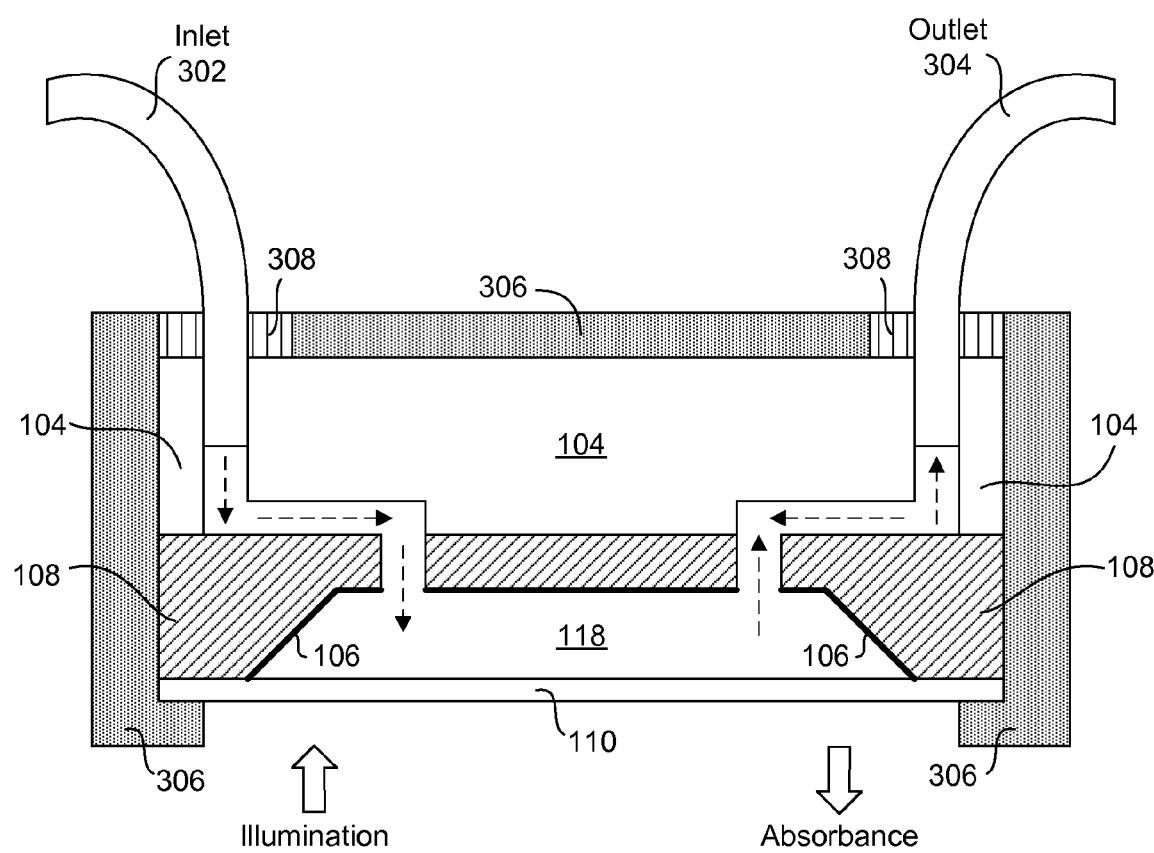
FIG. 3 shows an example integrated liquid handling package including the processed semiconductor device in accordance with embodiments of the present invention.

Referring now to FIG. 3, an example integrated liquid handling package including the processed semiconductor device in accordance with embodiments of the present invention is shown. Inlet 302 and/or outlet 304 may be coupled to multiple channels, where these pathways can be routed, and may be arranged in an array format to allow easy loading via robots (e.g., to accommodate standard distances for such loading). Polymer bounding layer 104 can be any suitable layer of soft or hard plastic (e.g., poly(dimethylsiloxane) ("PDMS")), epoxy, adhesive rubber or a metal, etc. The surface of the silicon device may also be oxidized by plasma enhanced chemical vapor deposition (PECVD) or electron beam evaporation. In addition, liquid handling package 306 can surround left and right edges of the structure, as well as covering the top portion along with sealing material 308 (e.g., epoxy, PDMS, rubber, glass, quartz, etc.).

In certain embodiments, mixing of a sample solution can be controlled for optical chamber 118 in order to observe real-time reactions of different chemicals and/or multiple components being pumped into the inlet at the same time. Further, inlet 302 and/or outlet 304 can involve any type of tubing, such as, for example tubing made of polymeric materials. The diameter of the via-holes may range from about 100 µm to about 1 mm.

In the detection or instrumentation module, absorbance and/or fluorescence of the supplied light can be analyzed. Typically, the fluorescence light is at higher wavelengths than the excitation light. Particular embodiments can also support photonic or multiphotonic excitation, where the excitation wavelengths are higher than the emission wavelengths, as well as epi-fluorescence applications that may utilize a separate filter.

Certain embodiments can also accommodate measurement of scattering light (e.g., X-ray small angle scattering spectroscopy), and may also take measurements using polarized light in circular dichrotomomy (CD) applications involving a measurement of the response degree of angle movement of the sample molecules. The fluorescence lifetimes can also be measured for Fourier transformed infrared (FTIR) applications, as well as Raman scattering, and luminescence.

SPR and nuclear magnetic resonance (NMR) spectroscopy can also be accommodated in particular embodiments. For such applications, the illumination window can receive optically pumped hyper polarized light, and such optical pumping, as well as the optical realization, can generally occur in close proximity. NMR may typically utilize a homogeneous field for measurement because this approach usually utilizes a metal coil, where the magnetic field can be reversed, and the optical pumping can be through chamber 118, where the magnetic field is around chamber 118. In this fashion, the microfluidic optical chamber can be optically activated.

Other electromagnetic sources can also be incorporated for manipulating the material sample in the microfluidic optical chamber. For example, particular embodiments can allow for manipulation of sample physical properties using thermal, electromagnetic, optical, dielectric, inhomogeneality, etc.

In particular embodiments, transparent window 110 can generally be relatively thin such that optical loss due to absorption in the window can be minimized (e.g., to under about 10%). Typical window implementations can be in a range of about 1-3 mm thick, whereas particular embodiments can allow for a thickness of from about 200 μm to about 300 μm. On the other hand, the opening width of the window may from 200 μm to 1 mm. Further, a transparent window in certain embodiments can be formed of any suitable material that is transparent to the spectrum of light (e.g., via light source 102) used in the system. For example, transparent window 110 can be made of plastic, glass, coc polymer, PDMS and/or any other suitable UV or visible light transparent materials. Thus, transparent window 110 may have a minimized height to reduce optical signal loss in either absorption or auto fluorescence.

In another embodiments, there can be as many as three transparent windows 110 distributed near the inlet, outlet and the center portion of the microfluidic chamber. The two windows near the inlet and outlet may serve as an optical pathway for illuminating and transmitting light into and out of the chamber. The window near the center of the chamber serves as the optical pathway for the fluorescence and scattering light emitted from the liquid sample in the microfluidic chamber. The three-window design allows for multiple functionality in the measurement of absorbance, fluorescence, phosphorous, photoluminescence, Rayleigh and Raman scattering light from the same microfluidic chamber device.

As shown in FIG. 3, the top surface of the silicon chip can include etched inlet and outlet reservoirs with guiding micro channels connected to the through holes. The liquid samples can be introduced from the inlet reservoir and guided into the via-hole. The liquid samples can then flow to the other side of the chips into the microscale optical chamber. Also, the liquid sample can be drawn out from microscale optical chamber 118 into outlet 304 by passing through another via-hole.

In one embodiment, two through-holes may be made inside micro channels across both surfaces of the silicon chip. Such holes can provide ducts for liquid sample flowing from one surface to another, such that that the liquid handling units can be installed on a side of the silicon chip other than the side where the microscale optical chambers are positioned. Without having the liquid handling units (e.g., reservoirs, connectors, tubings, or pumps) obstructing the microscale optical chamber, optical systems can have substantial exposure to chamber 118.

Also, chamber 118 in certain embodiments may be from about 1 cm to about 2 cm long to provide a relatively long light path. This approach allows for lower concentrations of materials needed for characterization. For example, as to absorption, a longer light path (e.g., about 2 cm) may double sensitivity relative to a typical light path length of about 1 cm. Thus, measurement flexibility can be increased for a given amount of material by using a relatively long light path channel. For fluorescence, the length of the light path can be very short, so that less light is lost in the light path. The reduced light attenuation associated with shorter light path can allow better sensitivity for fluorescence measurement. In addition, any suitable range for the length of chamber 118 can be formed in certain embodiments, such as ranging from about 1 cm to about 10 cm.

In certain embodiments the width of chamber 118 in may be from about 10 μm to about 500 μm long and the depth in certain embodiments may be from about 10 μm to about 200 μm to provide a microlitter or sub-microlitter volume. This approach allows for a reduction in volume and reduced consumption of materials needed for characterization. The chamber may hold a volume in the range of about 0.10 μL to 2 μL of fluid.

Another aspect of a particular embodiment of the invention involves the relatively strong thermal conducting nature of silicon material 104, thus allowing the temperature of chamber 118 to be controlled by coupling to a thermal device (heating and/or cooling). For example, a metal block or junction can be used to measure sample material not only at room temperature, but as low as from about 0° C. up to about 300° C., or as otherwise determined by the limits of the sample material itself. Thus, if a protein is active and in order to prevent denaturing at higher temperature, a sample measurement can be performed at about 37° C. In another embodiment, thermostable enzymes (e.g. Taq polymerase, and other thermal stable enzymes isolated or engineered from thermophilic microbes) can allow higher temperature (up to 99° C.) measurements. This type of measurement may not be possible with standard cuvettes without relatively bulky heating/cooling elements being coupled thereto.

In particular embodiments, such temperature control and an associated sensing unit can be integrated with the microfluidics optical device. For example, such an integrated temperature control and sensing unit can be a Peltier junction heater or metal line resistance heater. This approach can allow for thermocycling analysis of samples at varying temperatures, such as relatively low temperatures to prevent heat-denaturation of proteins, and higher temperatures for real-time genetic amplification using polymerase chain reactions (PCR).

In this fashion, measurement of chemical, biological, and/or physical reactions to temperature can be accommodated in chamber 118. Any temperature dependent characteristic can be isolated, such as measuring the melting point of chemicals for assessing chemical purity. Further, some applications may also include a camera. PCR can include a cycling temperature (e.g., between about 55° C. and about 95° C.), with observance of fluorescence in the reaction (e.g., about 10 ms per frame to about one second per frame) in order to observe a real-time PCR signal. In addition, any number of different enzymes such as nucleases, proteases, kinase, polymerase, glycosylase, topoisomerase, ligase, and phosphatases can also be measured using microfluidic optical chambers of particular embodiments.

Figure 4A:
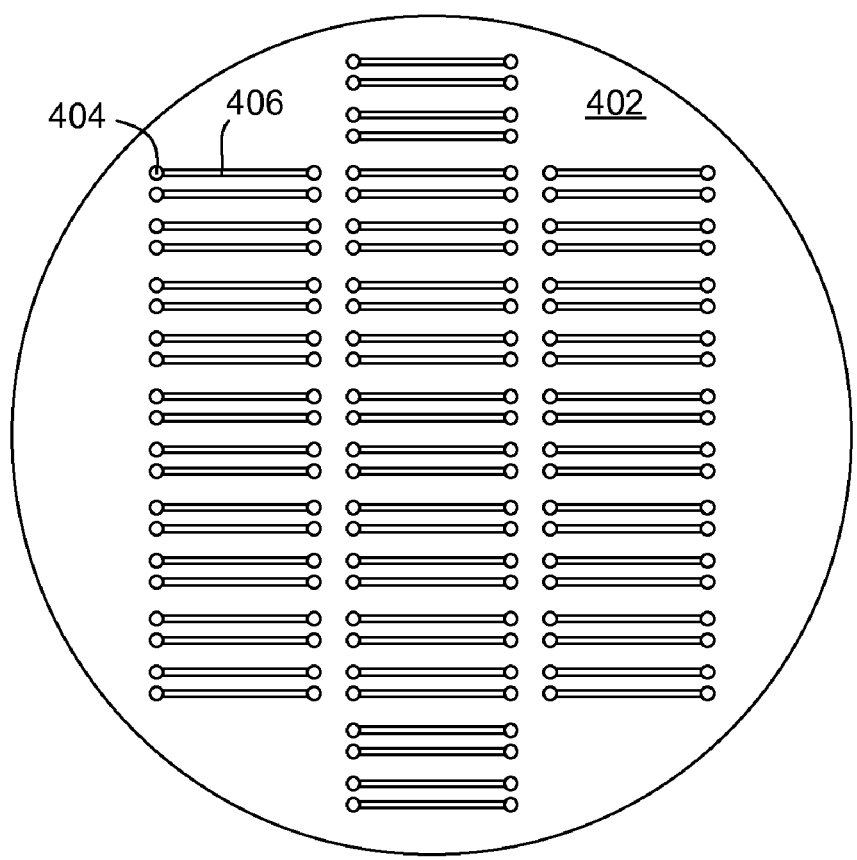
FIG. 4A shows an example top view of microfabrication masks for making two-channel devices in accordance with embodiments of the present invention.
Figure 4B:
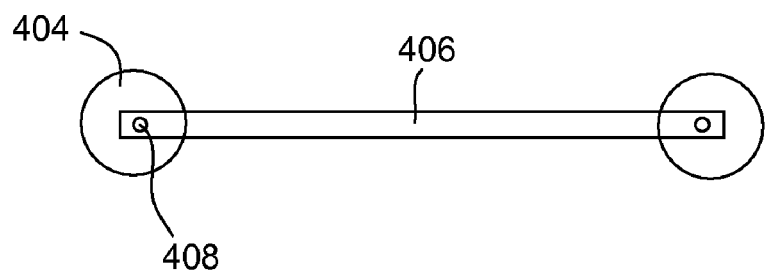
FIG. 4B shows an example close-up top view of mask structures for making a microfluidic optical device in accordance with embodiments of the present invention.

Referring now to FIG. 4A, an example top view of microfabrication masks for making two-channel devices in accordance with embodiments of the present invention is shown. In this example, a silicon wafer 402 can be defined with device masking, inlet/outlet reservoir 404 masking, microfluidic optical chamber 406 masking, and via-hole masking layers. As shown in the example close-up top view of the mask structures in FIG. 4B, via-hole masking layer 408 can be aligned with an edge of microfluidic optical chamber 406, and within inlet/outlet reservoir 404 masking layer.

Figure 5:
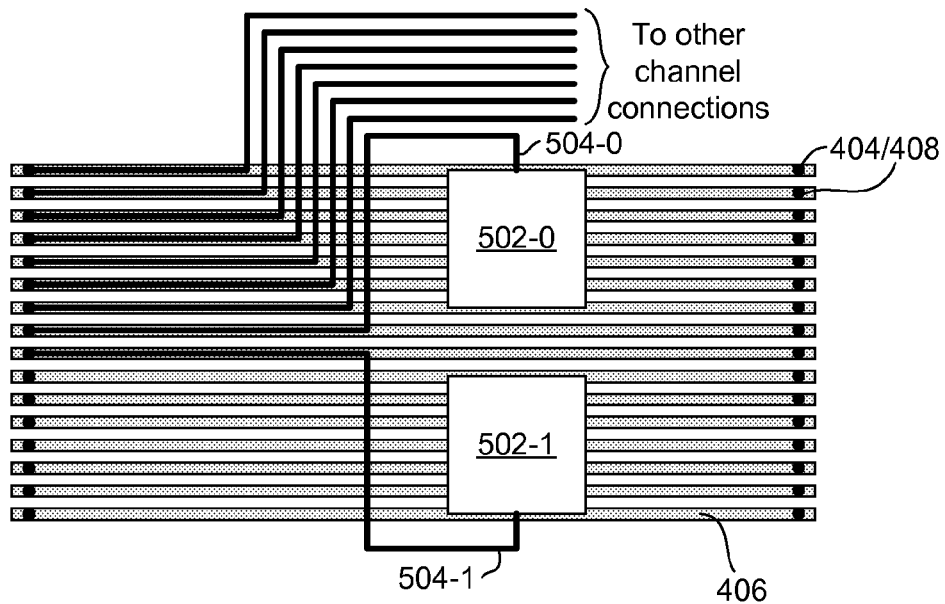
FIG. 5 shows example mask structures for making multiple channel devices in accordance with embodiments of the present invention.

Referring now to FIG. 5, example mask structures for making multiple channel devices in accordance with embodiments of the present invention are shown. Here, connections 504-0 and 504-1 can be made to external tubing portions 502-0 and 502-1, respectively. In such embodiments, the number of microchannels on each chip may be variable for different sample numbers that can be measured simultaneously. The channel number on one chip can be 1, 2, 4, 8, 16, 48, 96, 384, 768, 1536, etc. In the particular examples of FIGS. 4 and 5, photolithography masks for 2-channel and 96-channel chips are shown.

Figure 6:
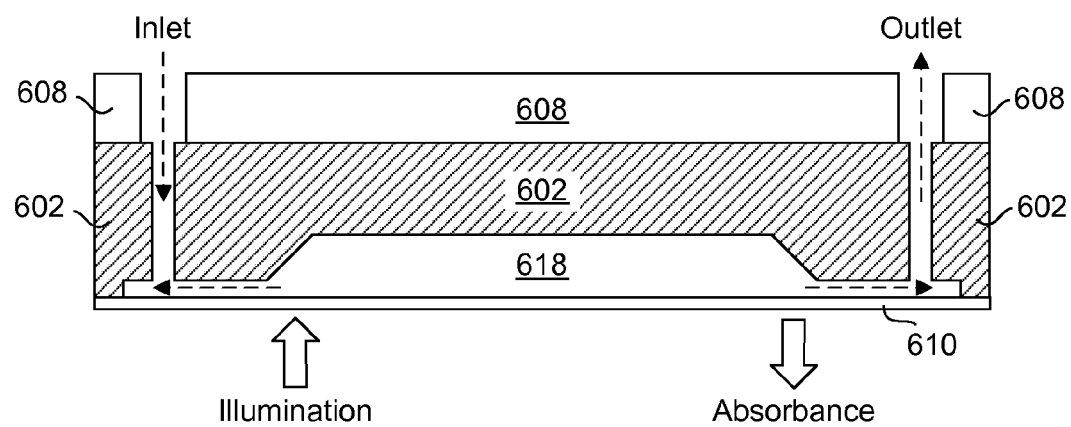
FIG. 6 shows an example cross-section of a two-level etched silicon microfluidic channel in accordance with embodiments of the present invention.

Referring now to FIG. 6, an example cross-section of a two-level etched silicon microfluidic channel in accordance with embodiments of the present invention is shown. In this particular example, microchannel 618 can have two levels in different depths, with the shallower level being connected to a top side of the chip through a via-hole, and the deeper level having the slanted reflective surfaces at both ends. Such a two-level design may be configured to prevent air bubbles trapped near the reflective surfaces. This approach can similarly use a semiconductor material (e.g., silicon) 602, as well as polymer bounding layer 608, and transparent windows 610.

Figure 7A:
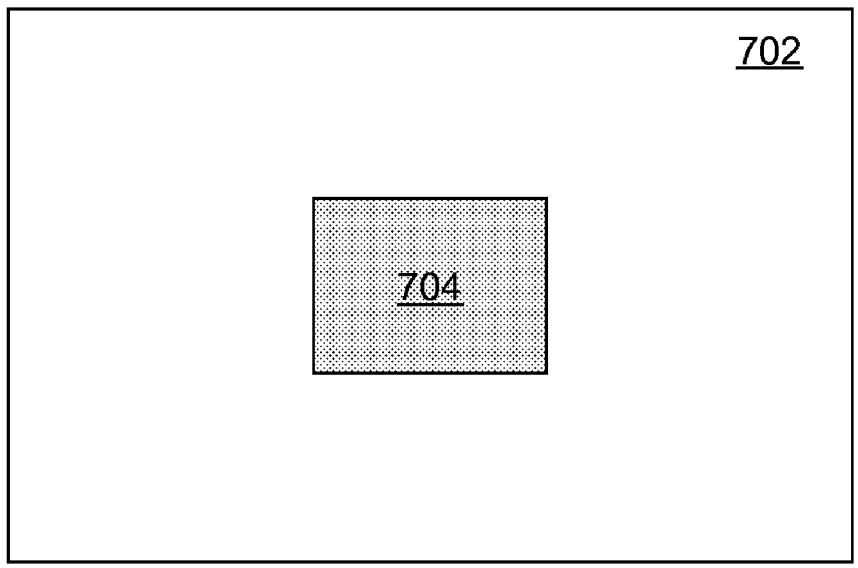
FIG. 7A shows an example top view of an integrated well plate and silicon microfluidic device structure in accordance with embodiments of the present invention.
Figure 7B:
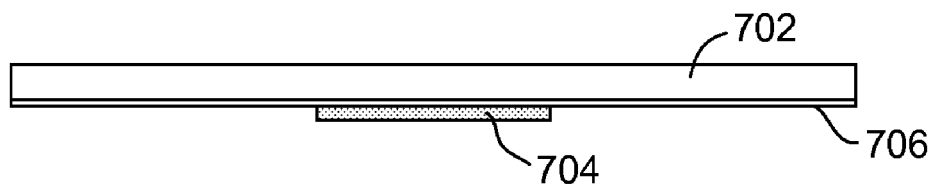
FIG. 7B shows a cross-section view of the example structure of FIG. 7A.

Referring now to FIG. 7A, an example top view of an integrated well plate and silicon microfluidic device structure in accordance with embodiments of the present invention is shown. FIG. 7B shows a cross-section view of the example structure of FIG. 7A. Silicon device 704 can be topped by microfluidic network layer (e.g., PDMS) 706, and well plate 702. Thus, such a multichannel version can have access holes through to the top of the structure for a microfluidic channel or routing layer. In this fashion, a microfluidics optical chip can be integrated with 96, 384, 1536, etc., micro well plates that may comply with standard micro well plate dimensions. The assembly of the microfluidics optical chip with the micro well plates may then be compatible with standard robotic liquid handling systems.

Figure 8:
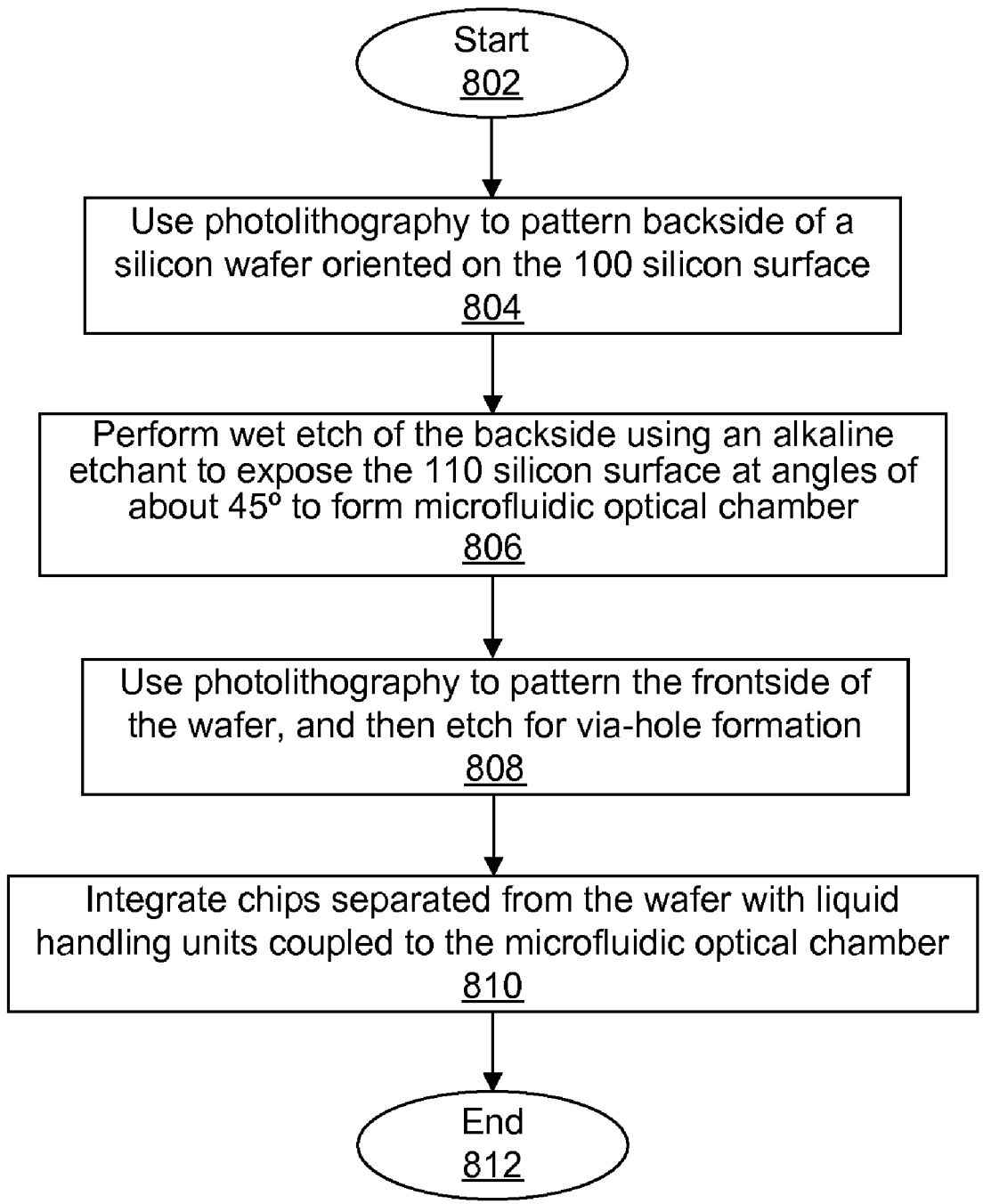
FIG. 8 shows an example processing flow for forming a microfluidic optical device in accordance with embodiments of the present invention.

Referring now to FIG. 8, an example processing flow for forming a microfluidic optical device in accordance with embodiments of the present invention is shown. The flow can begin (802), and photolithography may be utilized to pattern the backside of a silicon wafer that is oriented along the '100' silicon surface (804). Wet etching may then be performed on the backside (e.g., using an alkaline etchant) to expose, e.g., the '110' silicon surface at an angle of about 45° for forming a microfluidic optical chamber (806). The photolithography can also be used to pattern the frontside of the wafer, where etching can then be performed for via-hole formation (808). Chips separated from the wafer can then be integrated with liquid handling units coupled to the microfluidic optical chamber (810), completing the flow (812).

Figure 9:
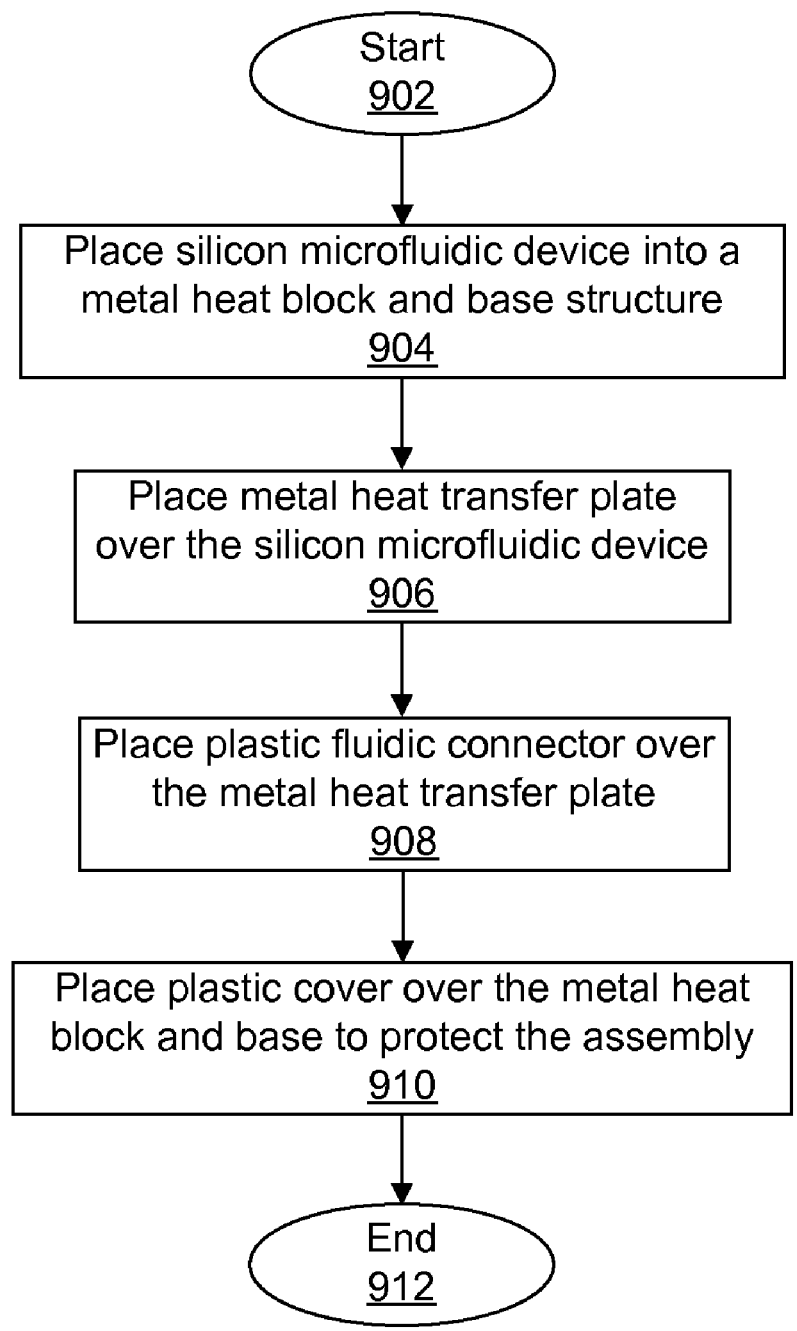
FIG. 9 shows an example flow for packaging a microfluidic optical device in accordance with embodiments of the present invention.

Referring now to FIG. 9, an example flow for packaging a microfluidic optical device in accordance with embodiments of the present invention is shown. The flow can begin (902), and a silicon microfluidic device may be placed into a metal heat block and base structure (904). A metal heat transfer plate may then be placed over the silicon microfluidic device (906). In this fashion, the metal heat transfer plate (e.g., a heat sink) may be connected to the microfluidics optical device such that the device can be rapidly cooled by way of transferring heat away from the chip portion. Further, the packaging material may have relatively high thermal conductivity, and can be in good contact with the silicon-based microfluidics chip. A plastic fluidic connector can then be placed over the metal heat transfer plate (908). A plastic cover can then be placed over the metal heat assembly block and base to protect (910) and complete (912) the assembly.

Figure 10:
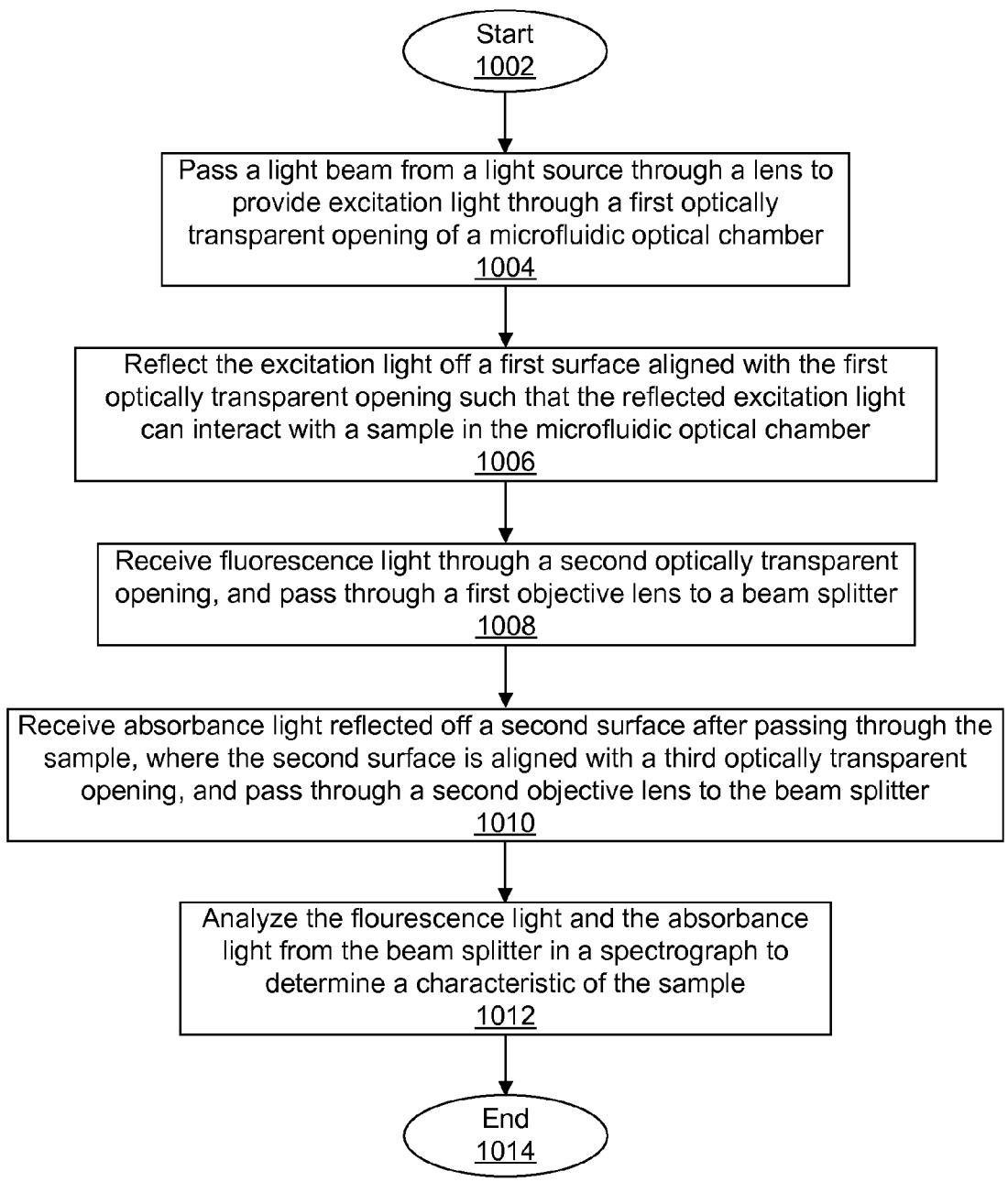
FIG. 10 shows an example flow for characterizing a liquid sample in accordance with embodiments of the present invention.

Referring now to FIG. 10, an example flow for characterizing a liquid sample in accordance with embodiments of the present invention is shown. The flow can begin (1002), and a light source may pass a beam through a lens to provide excitation light through a first optically transparent opening of a microfluidic optical chamber (1004). The excitation light can then be reflected off a first surface aligned with the first optically transparent opening such that the reflected excitation light can interact with a sample in the microfluidic optical chamber (1006). Fluorescence light can be received through a second optically transparent opening, and passed through a first objective lens to a beam splitter (1008). Absorbance light can also be received after being reflected off a second surface once passed through the sample, where the second surface is aligned with a third optically transparent opening, and where the absorbance light can then be passed through a second objective lens to the beam splitter (1010). A spectrograph can be used to analyze the fluorescence light and/or the absorbance light from the beam splitter in order to determine a characteristic of the sample (1012), thus completing the flow (1014).

Figure 11:
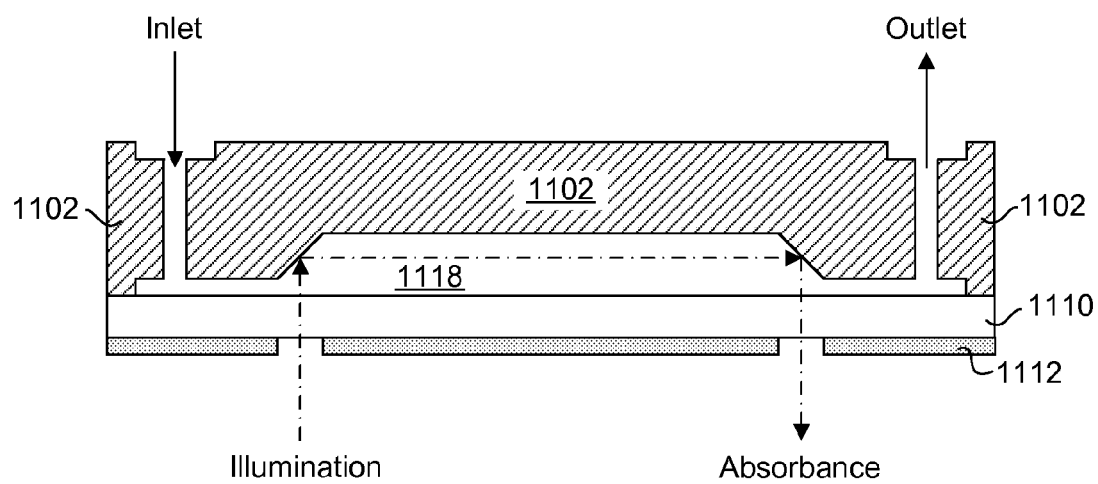
FIG. 11 shows an example microchip design with the through-wafer fluidic inlet and outlet pathways outside the optical detection chamber in accordance with embodiments of the present invention.

FIG. 11 shows an example microchip design with the through-wafer fluidic inlet and outlet pathways outside the optical detection chamber in accordance with embodiments of the present invention. In this particular example, microchannel 1118 can have two levels in different depths, with the shallower level being connected to a top side of the chip through a via-hole, and the deeper level having the slanted reflective surfaces at both ends. In such an arrangement, the via-hole opening on the microfluidics channel side may not affect the integrity of the optical chamber (e.g., microchannel 1118), and particularly the reflective surfaces (e.g., at 45° angles). This approach can similarly use a semiconductor material (e.g., silicon) 1102, as well as transparent window 1110, which can isolate the IC portion from the instrumentation portion, and material 1112 (e.g., $SiO_2$, polydimethylsiloxane (PDMS), coc polymer, or any UV transparent plastics) for coating transparent window 1110 to define optically transparent openings or through channels for light.

Figure 12:
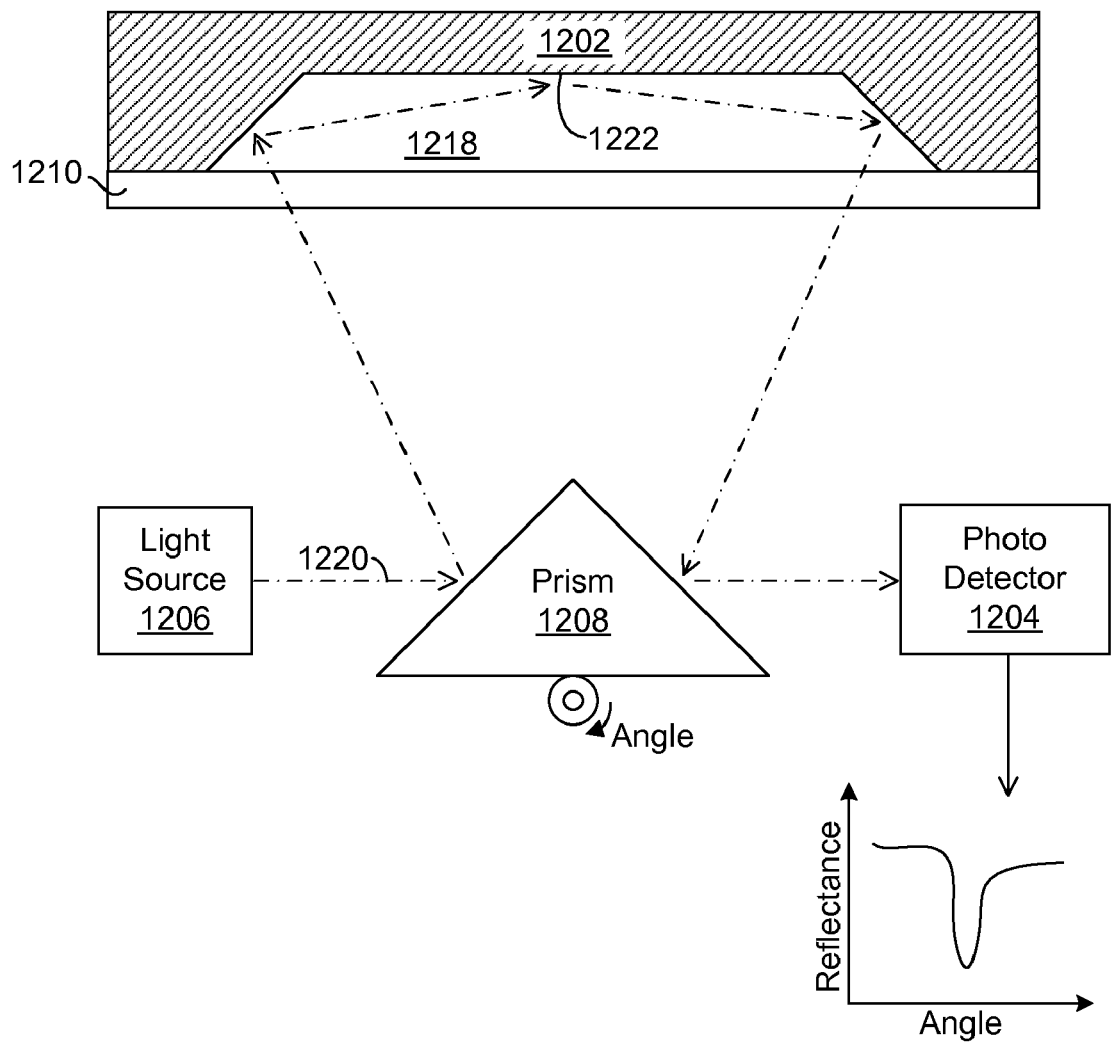
FIG. 12 shows an example surface plasmon resonance (SPR) spectroscopy system using an integrated microfluidic optical device in accordance with embodiments of the present invention.

FIG. 12 shows an example surface plasmon resonance (SPR) spectroscopy system using an integrated microfluidic optical device in accordance with embodiments of the present invention. A collimated broad band light beam 1220 (e.g., from light source 1206) can be reflected by a triangle or dove prism 1208, and illuminated through transparent window 1210 (e.g., transparent window 110) on the 45° angle reflective surface in microchannel 1218 (e.g., microfluidic optical chamber 118). This approach can similarly use a semiconductor material 1202 (e.g., the same or similar to material 108 described above). Because the incident angle is not perpendicular to the microfluidic channel, the light path is not parallel to the channel direction, and there can be a one time reflection on the channel bottom surface 1222. The channel bottom surface 1222 may be coated with a thin film of gold, and molecular probes may be tethered on the surface. When reagents flow through microchannel 1218 and react with the immobilized molecular probes, the SPR frequency of this gold thin film may shift. The frequency shift can be picked up by the external spectrometer or photo detector 1204.

Figure 13:
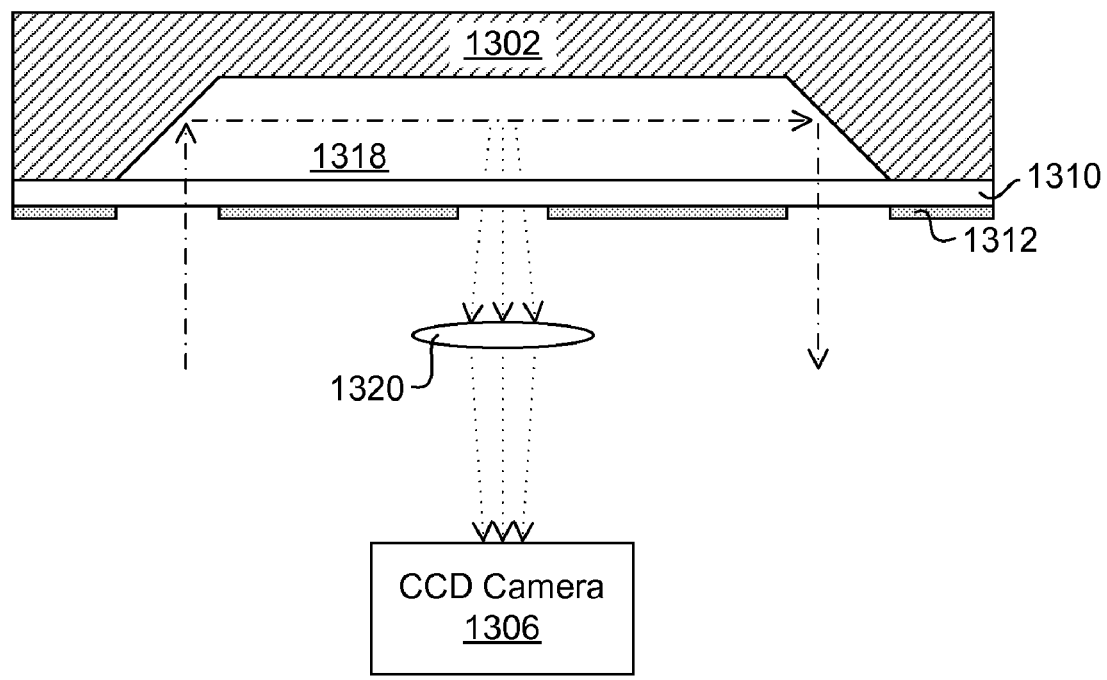
FIG. 13 shows an example dynamic particle optical scattering analysis system using a microfluidic optical device in accordance with embodiments of the present invention.

FIG. 13 shows an example dynamic particle optical scattering analysis system using a microfluidic optical device in accordance with embodiments of the present invention. The scattering light from small particles and biological cells can be measured in microfluidic optical channel 1318 (e.g., 118). As the scattering light emits from all directions, it can be detected from the center area of the microchannel via lens 1320 in charge-coupled device (CCD) camera 1306. Transparent window 1310 (e.g., 110) can isolate the IC portion from the instrumentation portion, and material 1312 (e.g., silicon dioxide, polydimethylsiloxane (PDMS), coc polymer, or any UV transparent plastics, and the same or similar to material 112) can be utilized to coat transparent window 1310 to define optically transparent openings or through channels for light. For example, this approach can also use a semiconductor material 1302 that is the same or similar to material 108 described above.

Figure 14:
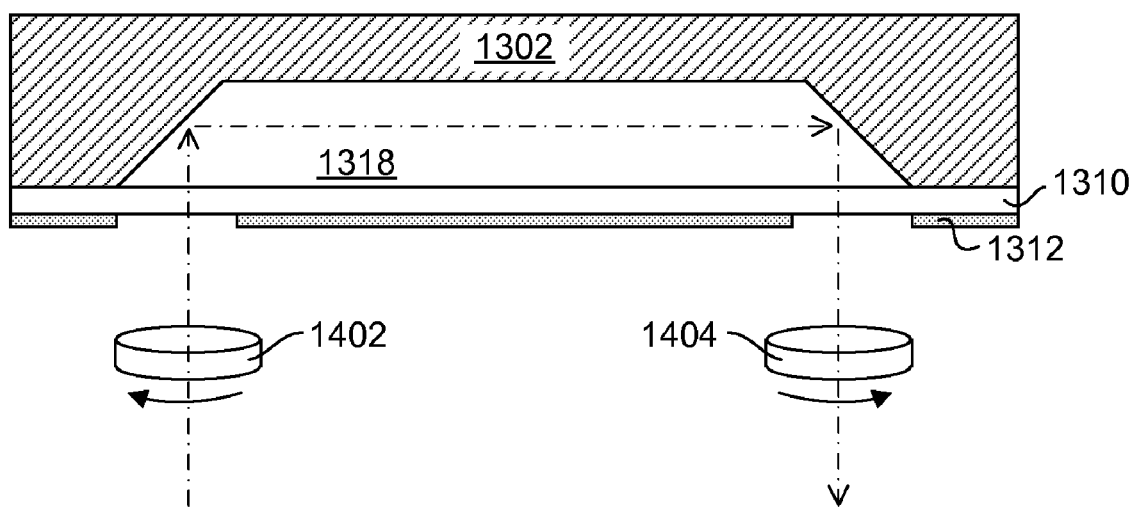
FIG. 14 shows an example molecule circular dichroism (CD) measurement system using a microfluidic optical device in accordance with embodiments of the present invention.

FIG. 14 shows an example molecule circular dichroism (CD) measurement system using a microfluidic optical device in accordance with embodiments of the present invention. Dichroism spectroscopy can be performed in the microfluidic optical chamber by introducing a circular polarizer (e.g., 1402) and analyzer (e.g., 1404) in the external optical spectroscopy system.

In certain embodiments, a digital light processing ("DLP") device can be used for fine adjustments of the light incident angle with computerized feedback control. For example, such a DLP can replace mirror 114 in the configuration shown in FIG. 1. This approach can be utilized to accommodate situations where the etched reflective surfaces (e.g., 106) have slight variations in slant angles and surface roughness.

In certain embodiments, the volume and depth of the microfluidics optical chambers can be changed by varying an associated etching time. The etch rate for the single crystal silicon may be about 1 µm per minute, so the etch depth can be well-controlled. For example, the chamber volume can range from about 1 nL to about 10 µL.

Also in certain embodiments, the surface of via-holes connecting the two sides of the chip can be modified with a self-assembly monolayer of chemical molecules configured to change the hydrophilicity and/or hydrophobicity. After surface modification, the liquid sample can flow more easily through the via-hole to another side of the chip. Various materials can be deposited on the surface using different techniques, such as chemical vapor deposition (CVD), oxidation, electroplating, polymer deposition, etc.

Particular embodiments can also involve biomolecules that are tethered to the surface. For example, such biomolecules can include nucleic acids (DNA and RNA), proteins, peptides, sugar/carbon hydrates, metabolites and small chemical compounds. Further, the surface-tethered biomolecules and chemical molecules can be patterned to form a microscale array of biochemical assay. Various biochemical libraries may also be deposited on the surface of the microfluidics optical chamber for combinatorial detection. Functional groups can include reactive groups. Functional groups can also include bifunctional crosslinkers having two reactive groups capable of forming a bond with two or more different functional targets (e.g., peptides, proteins, macromolecules, surface coating/surface, etc.). In some embodiments, the bifunctional crosslinkers are heterobifunctional crosslinkers with two different reactive groups. To allow covalent conjugation of biomolecule to the surface, suitable reactive groups include, e.g., thiol (—SH), carboxylate (COOH), carboxyl (—COOH), carbonyl, amine ($NH_2$), hydroxyl (—OH), aldehyde (—CHO), alcohol (ROH)ketone ($R_2CO$), active hydrogen, ester, sulfhydryl (SH), phosphate (—$PO_3$), or photoreactive moieties. Amine reactive groups can include, e.g., isothiocyanates, isocyanates, acyl azides, NHS esters, sulfonyl chlorides, aldehydes and glyoxals, epoxides and oxiranes, carbonates, arylating agents, imidoesters, carbodiimides, and anhydrides. Thiol-reactive groups include, e.g., haloacetyl and alkyl halide derivates, maleimides, aziridines, acryloyl derivatives, arylating agents, and thiol-disulfides exchange reagents. Carboxylate reactive groups include, e.g., diazoalkanes and diazoacetyl compounds, such as carbonyldiimidazoles and carbodiimides. Hydroxyl reactive groups include, e.g., epoxides and oxiranes, carbonyldiimidazole, oxidation with periodate, N,N'-disuccinimidyl carbonate or N-hydroxylsuccimidyl chloroformate, enzymatic oxidation, alkyl halogens, and isocyanates. Aldehyde and ketone reactive groups include, e.g., hydrazine derivatives for schiff base formation or reduction amination. Active hydrogen reactive groups include, e.g., diazonium derivatives for mannich condensation and iodination reactions. Photoreactive groups include, e.g., aryl azides and halogenated aryl azides, benzophenones, diazo compounds, and diazirine derivatives.

In one embodiment, a heterobifunctional crosslinker includes two different reactive groups that form a heterocyclic ring that can interact with a substrate peptide. For example, a heterobifunctional crosslinker, such as cysteine, may include an amine reactive group and a thiol-reactive group that can interact with an aldehyde on a derivatized peptide. Additional combinations of reactive groups for heterobifunctional crosslinkers include, e.g., amine- and sulfhydryl reactive groups, carbonyl and sulfhydryl reactive groups, amine and photoreactive groups, sulfhydryl and photoreactive groups, carbonyl and photoreactive groups, carboxylate and photoreactive groups, and arginine and photoreactive groups.

Also in particular embodiments, the microfluidic optical chip can be automatically transported and aligned with the spectroscopic imaging system. For example, such transportation and/or alignment may be controlled by a computer using optimization algorithms. Also, special markers can be included on the microfluidic chips, and may be used in automated pattern recognition.

Certain embodiments can also provide electrodes integrated into the channels such that a voltage potential can be applied across the microfluidics optical chamber to form a capillary electrophoresis system. For example, DNA and protein separation using electrophoresis and isoelectrical focusing can then be realized, and the optical spectra of the biomolecules can be monitored in real-time.

Also in certain embodiments, real-time kinetics, and not merely endpoints of the biochemical reactions in the microfluidic optical chamber 118, can be measured. Also, the liquid sample can be delivered into microfluidic optical chamber (e.g., 118) by relying on gravity or active pumping, such as peristaltic and piezoelectrical pumping.

Also in certain embodiments, the content within the microfluidic optical chamber can be gas phase material, rather than liquid. The optical properties of gas can be measured or monitored continuously in real-time. For example, concentration of particulates in the air can be monitored.

Definitions

By "protein" is meant a sequence of amino acids for which the chain length is sufficient to produce the higher levels of tertiary and/or quaternary structure. This is to distinguish from "peptides" or other small molecular weight drugs that do not have such structure. Typically, a protein will have a molecular weight of about 15-20 kD to about 20 kD.

The terms "peptide" and "peptidic compound" are used interchangeably herein to refer to a polymeric form of amino acids of from about 10 to about 50 amino acids (may consist of at least 10 and not more than 50 amino acids), which can comprise coded and non-coded amino acids, chemically or biochemically modified or derivatized amino acids, L- or D-amino acids, peptides having modified peptide backbones, and peptides comprising amino acid analogs. The amino acid may be limited to only amino acids naturally occurring in humans. The peptidic compounds may be polymers of: (a) naturally occurring amino acid residues; (b) non-naturally occurring amino acid residues, e.g., N-substituted glycines, amino acid substitutes, etc.; or (c) both naturally occurring and non-naturally occurring amino acid residues/substitutes. In other words, the subject peptidic compounds may be peptides or peptoids. Peptoid compounds and methods for their preparation are described in WO 91/19735, the disclosure of which is hereby incorporated in its entirety by reference herein. A peptide compound of the invention may comprise or consist of 23 amino acids or from 18 to 28 amino acids or from 20 to 26 amino acids. The active amino acid sequence of the invention comprises or consists of three motifs which may be overlapping, which are: an integrin binding motif sequence, a glycosaminoglycan binding motif sequence, and a calcium-binding motif.

The terms "treatment", "treating" and the like are used herein to refer to both therapeutic treatment and prophylactic or preventative measures. Those in need of treatment include those already with the disorder as well as those in which the disorder is to be prevented. In general, this encompasses obtaining a desired pharmacologic and/or physiologic effect, e.g., stimulation of angiogenesis. The effect may be prophylactic in terms of completely or partially preventing a disease or symptom thereof and/or may be therapeutic in terms of a partial or complete cure for a disease and/or adverse effect attributable to the disease. The terms as used herein cover any treatment of a disease in a mammal, particularly a human, and include: (a) preventing a disease or condition (e.g., preventing the loss of cartilage) from occurring in a subject who may be predisposed to the disease but has not yet been diagnosed as having it; (b) inhibiting the disease, e.g., arresting loss of cartilage; or (c) relieving the disease (e.g., enhancing the development of cartilage).

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the peptide. This includes chronic and acute disorders or diseases including those pathological conditions which predispose the mammal to the disorder in question. Non-limiting examples of disorders to be treated herein include skeletal loss or weakness and bone defects or breakage.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

That which is claimed is:

1. A method of characterizing a liquid sample, comprising:
    passing a light beam through a lens to provide excitation light through a first optically transparent opening of a microfluidic optical chamber;
    reflecting the excitation light off a first surface aligned with the first optically transparent opening such that the reflected excitation light interacts with the liquid sample;
    receiving fluorescence light through a second optically transparent opening, and passing the fluorescence light through a first objective lens to a beam splitter;
    receiving absorbance light reflected off a second surface after passing through the liquid sample, wherein the second surface is aligned with a third optically transparent opening, and passing the absorbance light through a second objective lens to the beam splitter; and
    analyzing the fluorescence light and the absorbance light from the beam splitter in a spectrograph to determine a characteristic of the liquid sample.

2. The method of claim 1, further comprising:
    adjusting a temperature of the liquid sample.

3. The method of claim 1, further comprising:
    adjusting a magnetic field surrounding the liquid sample.

* * * * *